(12) United States Patent
Cronenberg et al.

(10) Patent No.: US 9,623,184 B2
(45) Date of Patent: Apr. 18, 2017

(54) CARTRIDGE FOR CONTAINING AND DISPENSING A MEDICAMENT

(75) Inventors: Richard Cronenberg, Mahwah, NJ (US); Lionel Vedrine, Palo Alto, CA (US); Patrick Begley, Caldwell, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1215 days.

(21) Appl. No.: 13/513,087

(22) PCT Filed: Dec. 3, 2010

(86) PCT No.: PCT/US2010/003087
§ 371 (c)(1),
(2), (4) Date: Jul. 20, 2012

(87) PCT Pub. No.: WO2011/068544
PCT Pub. Date: Jun. 9, 2011

(65) Prior Publication Data
US 2012/0277684 A1 Nov. 1, 2012

Related U.S. Application Data

(60) Provisional application No. 61/266,616, filed on Dec. 4, 2009.

(51) Int. Cl.
*A61M 5/24* (2006.01)
*A61M 5/31* (2006.01)
(Continued)

(52) U.S. Cl.
CPC ............ *A61M 5/24* (2013.01); *A61M 5/2466* (2013.01); *A61M 5/28* (2013.01); *A61M 5/284* (2013.01);
(Continued)

(58) Field of Classification Search
CPC .......... A61M 5/24; A61M 5/284; A61M 5/28; A61M 5/3134; A61M 5/3135; A61M 2005/3132
See application file for complete search history.

(56) References Cited

U.S. PATENT DOCUMENTS 1,740,459 A * 12/1929 Hein ..................... A61M 5/344
604/242
4,254,768 A   3/1981 Ty
(Continued)

FOREIGN PATENT DOCUMENTS

EP    2022523 A1   2/2009
EP    1437150 B1   7/2013
(Continued)

*Primary Examiner* — Bradley Osinski
(74) *Attorney, Agent, or Firm* — Dickinson Wright PLLC

(57) ABSTRACT

A cartridge (100) for containing and dispensing a medicament, the cartridge (100) including a cartridge body (104) having an interior cavity (10B) therein, a stopper (112) movably disposed within the interior cavity (108), and a septum (116, 148) disposed at an opposite end of the interior cavity (108) from the stopper (112), for containing the medicament within the Interior cavity (108). The cartridge (100) also Includes a connection thread (120) integrally formed as a unitary construction of the cartridge body (104), the thread (120) being disposed at a first end of the cartridge body (104) for connecting a pen needle directly to the cartridge body (104) to pierce the septum (116, 148) and provide communication between the medicament and a patient end of the pen needle.

22 Claims, 9 Drawing Sheets

(51) Int. Cl.
*A61M 5/28* (2006.01)
*A61J 1/06* (2006.01)
*A61M 5/315* (2006.01)
*A61M 5/34* (2006.01)

(52) U.S. Cl.
CPC ........ *A61M 5/3134* (2013.01); *A61M 5/3135* (2013.01); *A61J 1/062* (2013.01); *A61M 5/2448* (2013.01); *A61M 5/31525* (2013.01); *A61M 5/31533* (2013.01); *A61M 5/347* (2013.01); *A61M 2005/2488* (2013.01); *A61M 2005/2492* (2013.01); *A61M 2005/3123* (2013.01); *A61M 2005/3132* (2013.01); *A61M 2005/31516* (2013.01); *Y10T 29/494* (2015.01)

(56) References Cited

U.S. PATENT DOCUMENTS

| | | | |
|---|---|---|---|
| 4,952,208 A | 8/1990 | Lix | |
| 5,019,053 A * | 5/1991 | Hoffman | A61M 5/28 604/220 |
| 5,192,270 A | 3/1993 | Carswell | |
| 5,242,405 A * | 9/1993 | Howe | A61M 5/3129 604/125 |
| 5,637,100 A | 6/1997 | Sudo | |
| 5,782,803 A * | 7/1998 | Jentzen | A61M 5/31511 604/110 |
| 6,382,568 B1 | 5/2002 | Snell | |
| 7,169,132 B2 | 1/2007 | Bendek et al. | |
| 7,556,614 B2 | 7/2009 | Griffiths et al. | |
| 7,678,079 B2 | 3/2010 | Shermer et al. | |
| 7,695,454 B2 | 4/2010 | Barron et al. | |
| 7,744,270 B2 | 6/2010 | Plishka et al. | |
| 8,403,883 B2 | 3/2013 | Fayyaz et al. | |
| 8,469,923 B2 | 6/2013 | Vedrine et al. | |
| 2001/0021820 A1 | 9/2001 | Lynn | |
| 2002/0045865 A1 | 4/2002 | Mitomi | |
| 2003/0212307 A1* | 11/2003 | Hladky | A61D 19/027 600/33 |
| 2004/0236273 A1* | 11/2004 | Tanaka | A61M 5/284 604/89 |
| 2006/0100575 A1 | 5/2006 | Restelli et al. | |
| 2007/0270743 A1* | 11/2007 | Ackerman | A61M 5/3243 604/110 |
| 2008/0082044 A1 | 4/2008 | Sharon et al. | |
| 2008/0116105 A1 | 5/2008 | Statham | |
| 2008/0215004 A1 | 9/2008 | Harding et al. | |
| 2008/0215015 A1 | 9/2008 | Cindrich et al. | |
| 2008/0255521 A1 | 10/2008 | Kubo | |
| 2009/0036837 A1 | 2/2009 | Kakiuchi et al. | |
| 2011/0092917 A1 | 4/2011 | Wei et al. | |

FOREIGN PATENT DOCUMENTS

| | | |
|---|---|---|
| JP | 06-209994 | 8/1994 |
| JP | H0780064 A | 3/1995 |
| JP | 2000070366 A | 3/2000 |
| JP | 2000-237310 | 9/2000 |
| JP | 2002509469 A | 3/2002 |
| WO | WO2005039676 A1 | 5/2005 |
| WO | WO2009043000 A1 | 4/2009 |
| WO | WO2009137486 A1 | 11/2009 |
| WO | WO2010033778 A2 | 3/2010 |

* cited by examiner

CARTRIDGE FOR CONTAINING AND DISPENSING A MEDICAMENT

CROSS-REFERENCE TO RELATED APPLICATION

This application claims the benefit of U.S. Provisional Patent Application Ser. No. 61/266,616, filed Dec. 4, 2009 at the U.S. Patent and Trademark Office, the disclosure of which is incorporated herein by reference in its entirety.

FIELD OF THE INVENTION

The present invention relates generally to a cartridge for containing and dispensing a medicament, and more particularly to a cartridge for containing and dispensing a medicament in conjunction with a pen injection device.

BACKGROUND OF THE INVENTION

Medication delivery pens are hypodermic syringes used for self-injection of precisely measured doses of medication. Pens are widely used, for example, by diabetics to self-inject insulin. A typical prior art medication delivery pen includes a cartridge which contains a volume of liquid medication sufficient for several doses. The dose is injected into a tissue area, such as the intramuscular tissue layer, the subcutaneous tissue layer, or the intradermal tissue layer.

The assembly and operation of a typical pen injection device is described in commonly-assigned U.S. Pat. No. 7,645,264, issued on Jan. 12, 2010, which is incorporated herein by reference in its entirety.

Pen injection devices, such as the exemplary pen injector 50, as shown in FIGS. 1 and 2, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is employed by the user to securely hold the pen injector 50 in a shirt pocket, purse, or other suitable location.

FIG. 2 is an exploded view of the exemplary drug delivery pen 50 shown in FIG. 1. The dose knob/button 24 has a dual purpose and is used to both set the dosage of the medication to be injected and to inject the dosed medicament via a lead screw 7 and stopper 15 from a medicament cartridge 12, which is attached to the drug delivery pen through a lower housing 17. The lower housing 17 typically has dosage indicia on the exterior thereof. The medicament cartridge 12 is typically a glass tube sealed at one end with a septum 16 and at the other end with the stopper 15. In standard drug delivery pens, the dosing and delivery mechanisms are all found within the outer sleeve 13. Those mechanisms are not described in greater detail here as they are understood by those knowledgeable of the art.

A pen needle 10 includes a hub 20, a patient needle 11 extending from a patient end of the pen needle, and a septum-penetrating needle cannula 18 disposed within the hub 20 on a non-patient side thereof. The septum-penetrating needle cannula 18 is in fluid communication with the patient needle 11. The hub 20 is preferably screwed onto the lower housing 17. In attaching the hub 20 to the lower housing 17, the septum-penetrating cannula 18 pierces the septum 16, but the septum 16 does not move with respect to the medicament cartridge 12. The stopper 15, however, is axially displaceable within the medicament cartridge 12 while maintaining a fluid tight seal. The distal movement of the plunger or stopper 15 within the medicament cartridge 12 (due to advancement of the lead screw 7) causes medication to be forced into the patient needle 11 of the hub 20.

To protect a user, or anyone who handles the pen needle assembly 10, an outer shield 29, which attaches to the hub 20, covers the hub 20. The outer shield 29 can also be used as a handle or grip to screw hub 20 onto or off pen injector 50. An inner shield 28 covers the patient needle 11 within the outer shield 29. The inner shield 28 can be secured to the hub 20 to cover the patient needle 11 by any suitable means, such as an interference fit or a snap fit. The outer shield 29 and inner shield 28 are removed prior to use. The cap 21 fits snugly against outer sleeve 13 to allow a user to securely carry the pen injection device 50.

FIG. 3 is a cross-sectional view of an exemplary cartridge 76 and a lower housing or cartridge retainer 78 for a drug delivery pen, such as the pen injector 50. As shown in FIG. 3, opposing ends of cartridge retainer 78 include threads 80 and 82 for respectively connecting the cartridge retainer 78 to pen needle assembly 10 and the outer sleeve 13. The lower housing 80 may be made of, for example, plastic. The cartridge 76 may be made of, for example, glass.

A stopper 84 is movably disposed within an interior cavity of the cartridge 76. The stopper 84 is shown in phantom lines in a position for the beginning of an injection, and is shown in cross section in a position representing the end of the useful life of the cartridge 76. In other words, no more medicament 86 can be ejected from the cartridge 76. More specifically, the leading surface of the stopper 84 forms a substantially right angle with the side thereof. And during blowing or other elongation of the glass to form the cartridge 76, an end 88 of the interior cavity of the cartridge is radiused. Therefore, the stopper 84 can only be moved a certain distance in the interior cavity before the radius of the end 88 prevents further movement of the stopper 84. Accordingly, an uninjectable, or dead volume of medicament remains in the cartridge 76.

A septum 92 is held on the end of the cartridge 76 by a crimping ring or band of metal 94. The septum 92 is made of, for example, rubber and the crimping ring 94 is made of, for example, aluminum or plastic. During installation of the septum 92 and crimping of the crimping ring 94, particles from the septum 92 and/or the crimping ring 94 may be generated and may enter the interior cavity of the cartridge 76.

SUMMARY OF THE INVENTION

An aspect of the present invention is to provide cartridge for containing and dispensing a medicament in which the need for a cartridge retainer is obviated.

The foregoing and/or other aspects of the present invention are achieved by providing a cartridge for containing and dispensing a medicament, the cartridge including a cartridge body having an interior cavity therein, a stopper movably disposed within the interior cavity, and a septum disposed at an opposite end of the cavity from the stopper for containing the medicament within the cavity. The cartridge also includes a connection thread integrally formed as a unitary construction with the cartridge body, the thread being disposed at a first end of the cartridge body for connecting a pen needle directly to the cartridge body to pierce the septum and provide communication between the medicament and a patient end of the pen needle. The cartridge additionally includes a connector for directly connecting the cartridge body to a dosing mechanism for moving the stopper toward the septum to dispense the medicament.

The foregoing and/or other aspects of the present invention are also achieved by providing a cartridge for containing and dispensing a medicament, the cartridge including a cartridge body having an interior cavity therein, a stopper movably disposed within the interior cavity, and a septum disposed at an opposite end of the cavity than the stopper for containing the medicament within the cavity. The cartridge also includes septum disposed at an opposite end of the cavity from the stopper for containing the medicament within the cavity. The cartridge additionally includes connector means for directly connecting the cartridge body to a dosing mechanism for moving the stopper toward the septum to dispense the medicament, and dosage indicia disposed directly on the cartridge body. An end of the stopper closest to the septum has a shape corresponding to a shape of an end of the interior cavity closest to the septum for minimizing an uninjectable volume of medicament. The cartridge body comprises at least one passageway for venting from the interior cavity during lyophilization subsequent to at least partial insertion of the stopper into the interior cavity.

The foregoing and/or other aspects of the present invention are also achieved by providing a method of manufacturing a cartridge for containing and dispensing a medicament, the method including forming a cartridge body having an interior cavity therein, forming connection threads on a first end of the cartridge body for connecting a pen needle directly to the cartridge body, inserting a stopper into the interior cavity to be movable therein, and forming a connector on the cartridge body for connecting the cartridge body directly to a dosing mechanism for moving the stopper toward the septum to dispense the medicament.

Additional and/or other aspects and advantages of the present invention will be set forth in part in the description that follows and, in part, will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which.

DETAILED DESCRIPTION OF EXEMPLARY EMBODIMENTS

Figure 1:
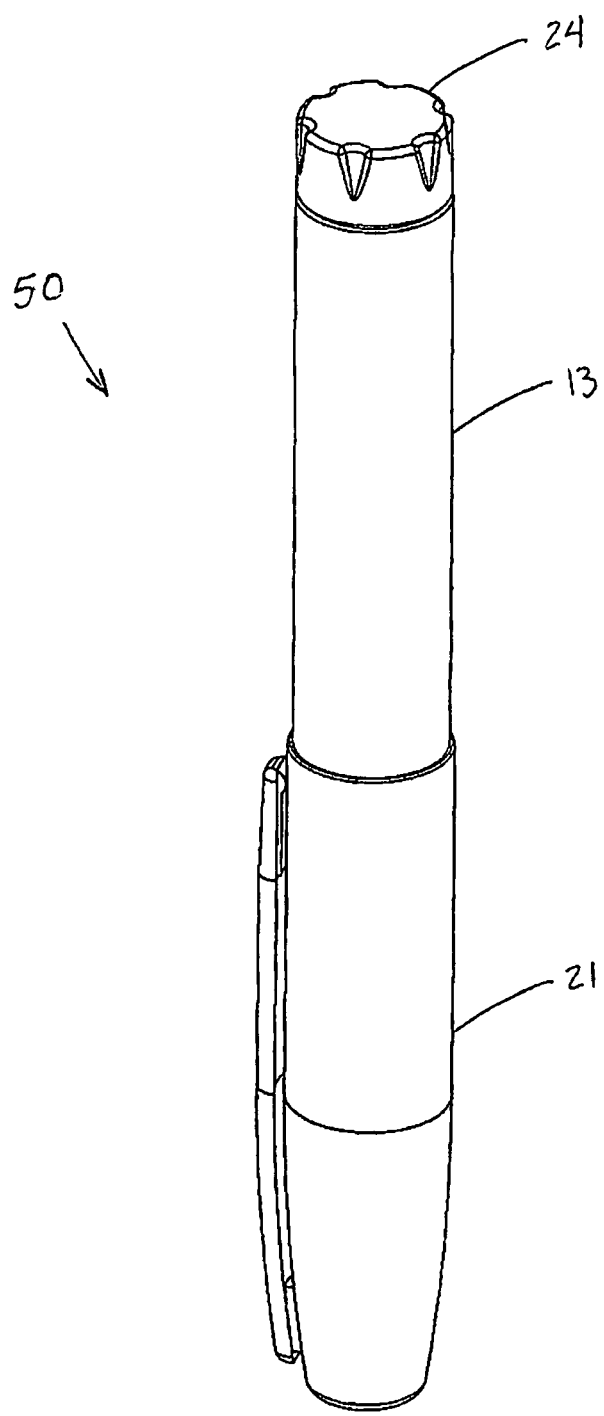
FIG. 1 is a perspective view of an exemplary drug delivery pen.
Figure 2:
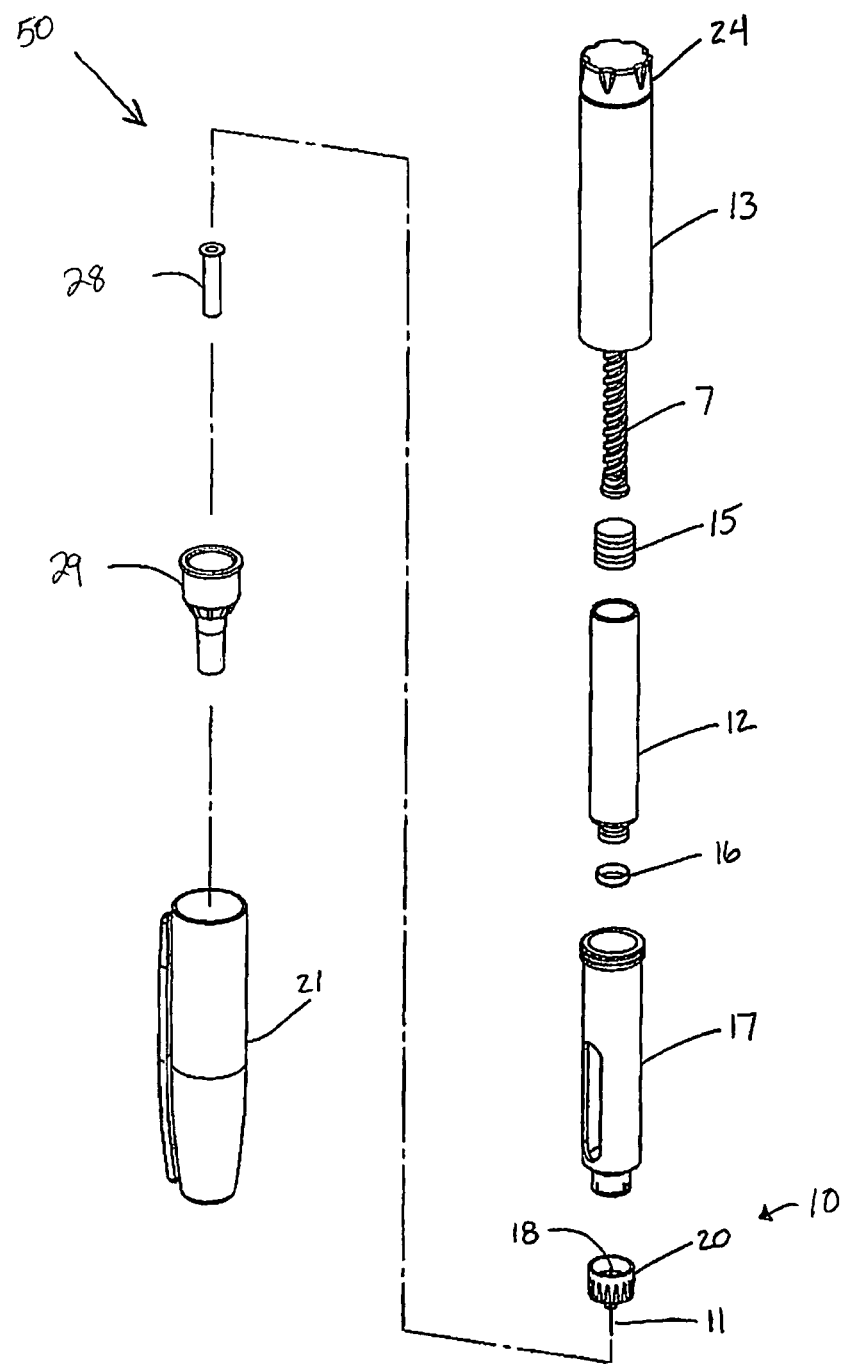
FIG. 2 is an exploded view of the exemplary drug delivery pen of FIG. 1.
Figure 3:
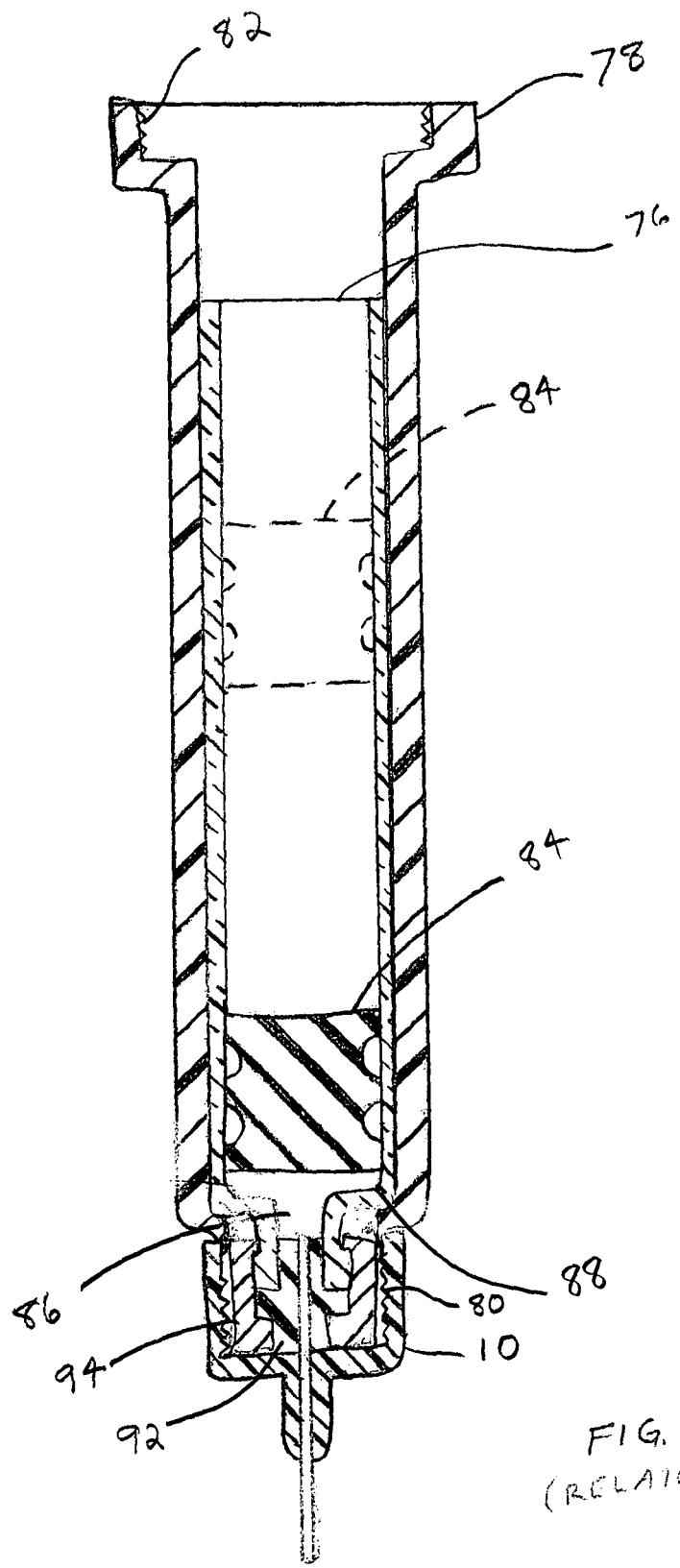
FIG. 3 is a cross-sectional view of an exemplary cartridge for a drug delivery pen.

Reference will now be made in detail to embodiments of the present invention, examples of which are illustrated in the accompanying drawings, wherein like reference numerals refer to the like elements throughout. The descriptions of these embodiments exemplify the present invention by referring to the drawings.

Figure 4:
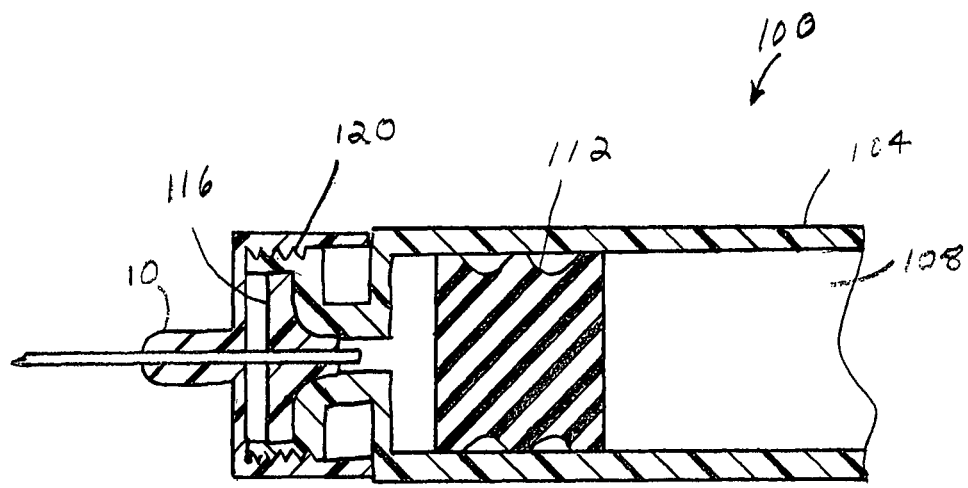
FIG. 4 is a partial cross-sectional view illustrating integrated threads of a cartridge in accordance with an embodiment of the present invention.

FIG. 4 is a partial cross-sectional view of a cartridge 100 for containing and dispensing a medicament in accordance with an embodiment of the present invention. As shown in FIG. 4, the cartridge 100 includes a transparent cartridge body or body 104 that has an interior cavity 108 and a stopper 112 movably disposed therein. As discussed in greater detail below, the cartridge body 104 also has a septum 116 disposed at a front or user end thereof.

At the front end, the cartridge 100 additionally has at least one connection thread 120 for connecting a pen needle assembly 10 directly to the cartridge body 104. For brevity, the pen needle assembly 10 will hereinafter be referred to as the pen needle 10. According to one embodiment, the body 104 is made of clear glass that does not react with the medicament. According to another embodiment, the body 104 is made of a transparent plastic material that does not react with the medicament. Examples of such a plastic material include, but are not limited to, cyclic olefin polymer (COP) and cyclic olefin copolymer (COC). One example of a COC is available from Zeon Chemicals, L.P., of Louisville, Ky. under the designation "BD CCP Resin," and is listed by the U.S. Food and Drug Administration and DMF No. 16368. In addition, according to one embodiment, the body 104 is molded and the connection thread 120 is molded on the body 104 to be integrally formed as a unitary construction with the body 104.

Because the pen needle 10 is connected directly to the body 104, it is not necessary to have a vial container or cartridge container, such as cartridge container 78, disposed between the body 104 and the pen needle 10. Therefore, a tolerance for the pen needle connection can be reduced. In other words, because the connection between the pen needle 10 and the body 104 is direct, without having to account for an intervening part, a looser fit between the pen needle 10 and the body 104 may be acceptable. Because users may have limited digital dexterity due to medical conditions, such as diabetes, this looser tolerance is beneficial in assembling the pen needle 10 to the cartridge body 104. According to one embodiment, the connection thread 120 is male. According to another embodiment, the connection thread 120 is female.

Figure 5:
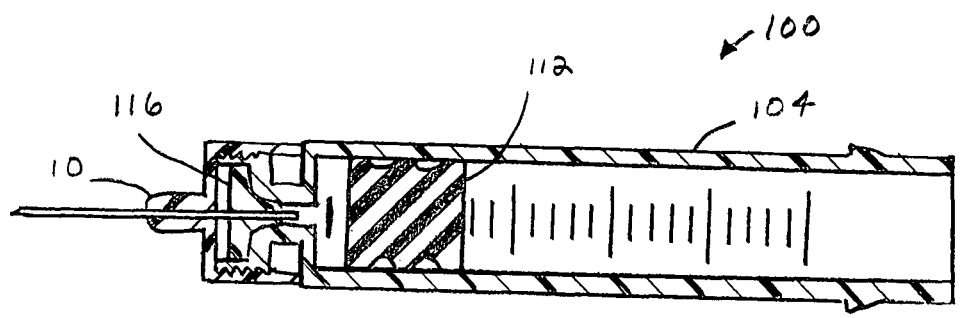
FIG. 5 is a cross-sectional view illustrating a septum of a cartridge in accordance with an embodiment of the present invention.

As shown in FIG. 5, according to one embodiment, the septum 116 is made of an elastomeric material, such as rubber, that does not react with the medicament and is adhered directly to the body 104. Preferably, the material for the septum 116 has a self-sealing or self-healing property, allowing multiple punctures and resealings for successive connection of one or more pen needles 10. According to one embodiment, an adhesive is used to adhere the septum 116 to the body 104. According to another embodiment, the septum is made of a material that has an "adhesion" property that is compatible with the material of the body 104, so that the septum 116 can be co-injected with the body 104 during the molding thereof. In other words, the septum 116 is adhered to the body 104 during a molding process, thereby integrally forming the body 104 and the septum 116 as a unitary construction. According to yet another embodiment, the body 104 and the septum 116 are molded of the same material. Such a septum 116 that is adhered to the body 104 obviates the need for a crimping ring, such as crimping ring 94, and therefore eliminates the chance of particles entering the interior cavity 108 during a crimping process.

Figure 6:
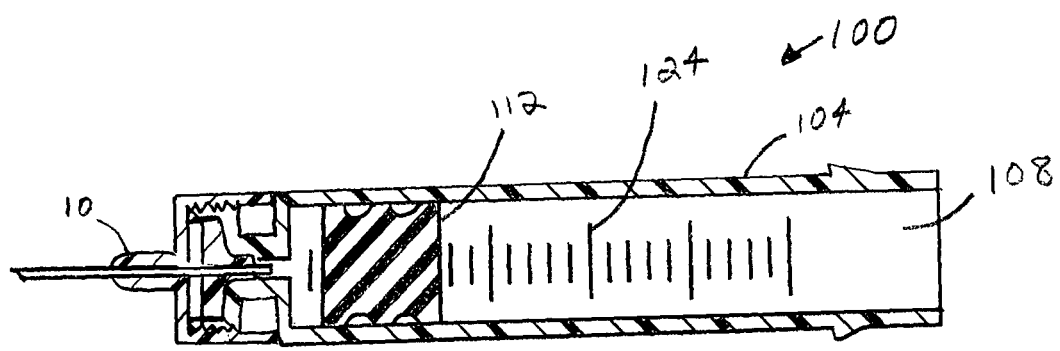
FIG. 6 is a cross-sectional view illustrating dosage indicia on a cartridge in accordance with an embodiment of the present invention.

FIG. 6 is a cross-sectional view illustrating dosage or volume indicia 124 disposed directly on the cartridge body 104. According to one embodiment, the dosage indicia 124 are "printed" directly on the body 104 using ink. According to another embodiment, the dosage indicia 124 are etched on the body 104.

Using a plastic material represents a good alternative because of the precision achievable during molding. According to one embodiment, dosage indicia 124 are etched into the mold used for molding the body 104, and the dosage indicia 124 are formed on the body 104 during the molding process. According to another embodiment, an additive can be added to the plastic material of the body 104, so that the dosage indicia 124 can be formed by, for example, laser etching.

Figure 7:
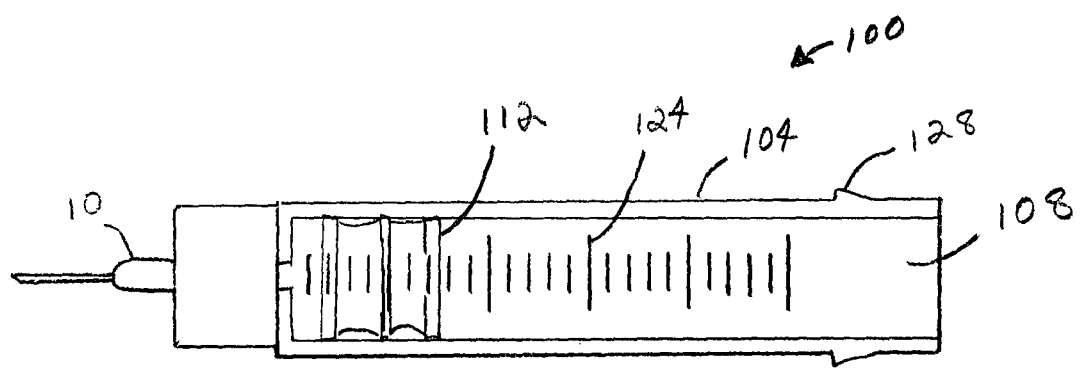
FIG. 7 is a perspective view of the cartridge of FIG. 6.

FIG. 7 is a perspective view of the cartridge 100 illustrating a preferred embodiment in which the body 104 is transparent, and thus the stopper 112, which is disposed in the interior cavity 108, is visible through the wall of the body 104. Progress of the stopper with respect to the dosage indicia 124 through the interior cavity 108, indicates a remaining volume of medicament.

Figure 8:
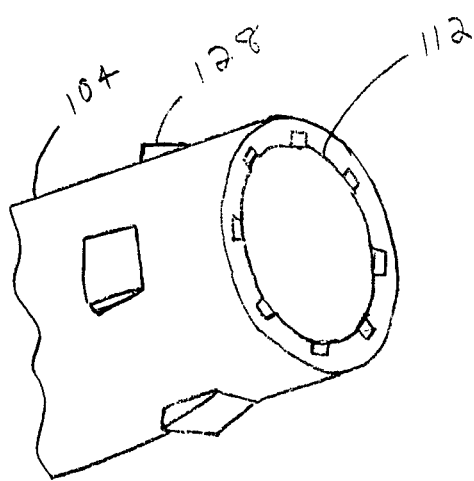
FIG. 8 is a perspective view of a first embodiment of an attachment mechanism for a cartridge in accordance with an embodiment of the present invention.
Figure 9:
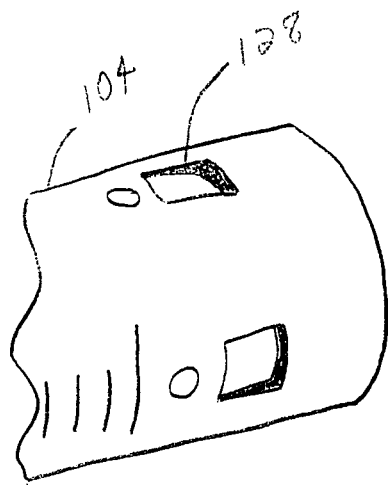
FIG. 9 is a perspective view of a second embodiment of an attachment mechanism for a cartridge in accordance with an embodiment of the present invention.

FIG. 7 (in addition to FIGS. 5 and 6) illustrates a connector 128 for directly connecting the cartridge body 104 to a dosing mechanism, such as an autoinjector, a spring driver, a manual driver, or the dosing mechanism contained in the outer sleeve 13 of the pen injector 50. As shown in FIG. 7, the connector 128 is disposed directly on the body 104. FIGS. 8-13 respectively illustrate first through sixth embodiments of connectors 128. As shown in FIGS. 7 and 8, according to one embodiment, the connector 128 includes a male protrusion disposed on the body 104. The wedge-shaped male protrusion corresponds to a female recess disposed on the dosing mechanism. The combination of the male protrusion and the female recess provides a snap-fit connection between the cartridge body 104 and the dosing mechanism. Conversely, FIG. 9 illustrates an embodiment in which the connector 128 includes a female recess disposed on the body 104. The female recess corresponds to a male protrusion disposed on the dosing mechanism to provide a snap-fit connection between the cartridge body 104 and the dosing mechanism.

Figure 10:
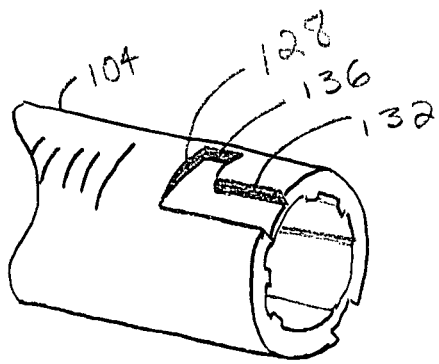
FIG. 10 is a perspective view of a third embodiment of an attachment mechanism for a cartridge in accordance with an embodiment of the present invention.
Figure 11:
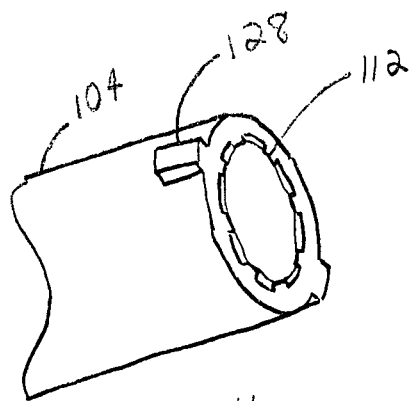
FIG. 11 is a perspective view of a fourth embodiment of an attachment mechanism for a cartridge in accordance with an embodiment of the present invention.

FIGS. 10 and 11 illustrate alternative connectors 128. In FIG. 10, the connector 128 includes a linear slot 132 disposed axially on the body 104. The connector 128 illustrated in FIG. 10 also includes a radial portion 136 disposed at an end of the axial slot 132 to form an L-shaped slot in combination with the axial slot 132. FIG. 11 illustrates an embodiment in which the connector 128 includes a linear protrusion that is substantially axially aligned on the body 104. In the embodiment of FIG. 10, an axially aligned linear protrusion similar to that shown in FIG. 11 is disposed on the dosing mechanism. Conversely, in the embodiment of FIG. 11, either a linear slot or and L-shaped slot similar to that shown in FIG. 10 is disposed on the dosing mechanism. To connect the body 104 to the dosing mechanism in the embodiments of FIGS. 10 and 11, the linear protrusion is inserted into the linear slot. And in the embodiments including the radial portion (for example, radial portion 136), the body 104 and the dosing mechanism are additionally rotated axially with respect to each other to engage the linear protrusion in the radial portion, thereby selectively locking the body 104 to the dosing mechanism.

Figure 12:
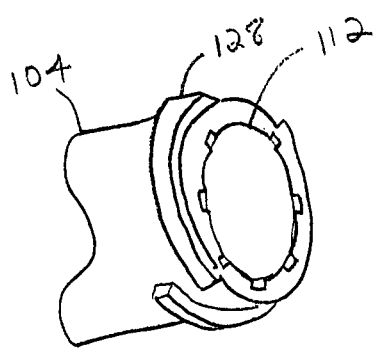
FIG. 12 is a perspective view of a fifth embodiment of an attachment mechanism for a cartridge in accordance with an embodiment of the present invention.
Figure 13:
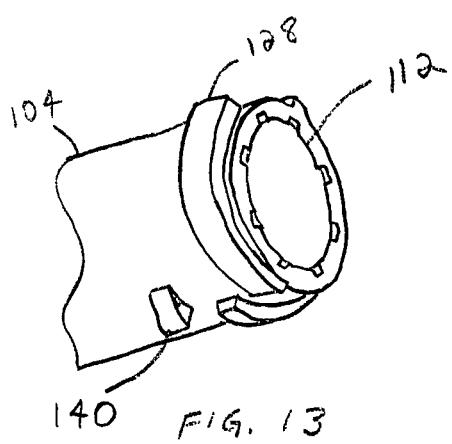
FIG. 13 is a perspective view of a sixth embodiment of an attachment mechanism for a cartridge in accordance with an embodiment of the present invention.

In the embodiment shown in FIG. 12, the connector 128 includes a male thread. In such an embodiment, the dosing mechanism includes a corresponding female thread for attaching the body 104 thereto. In FIG. 13, in addition to the male thread, the connector 128 additionally includes an anti-disassembly feature 140. According to the embodiment shown in FIG. 13, the anti-disassembly feature 140 includes a radially aligned wedge shape. In such an embodiment, in addition to a female thread, the dosing mechanism includes a radially oriented female recess (or series of female recesses to form a ratchet) to provide a snap-fit in combination with the radially aligned wedge shape 140. As will be appreciated by one skilled in the art, the male thread may be disposed on the dosing mechanism and the corresponding female thread may be disposed on the body 104 without departing from the scope of the present invention. Similarly, the wedge shape may be disposed on the dosing mechanism and the corresponding female recess(es) may be disposed on the body 104 without departing from the scope of the present invention. Additionally, one skilled in the art will appreciated that the connector 128 is not limited to the embodiments shown in FIGS. 8-13.

The combination of the integral connection thread 120 and the connector 128 obviates the need for a cartridge retainer, such as cartridge retainer 78. The dosage indicia 124 on the cartridge body 104 further obviate the need for such a cartridge retainer.

Figure 14:
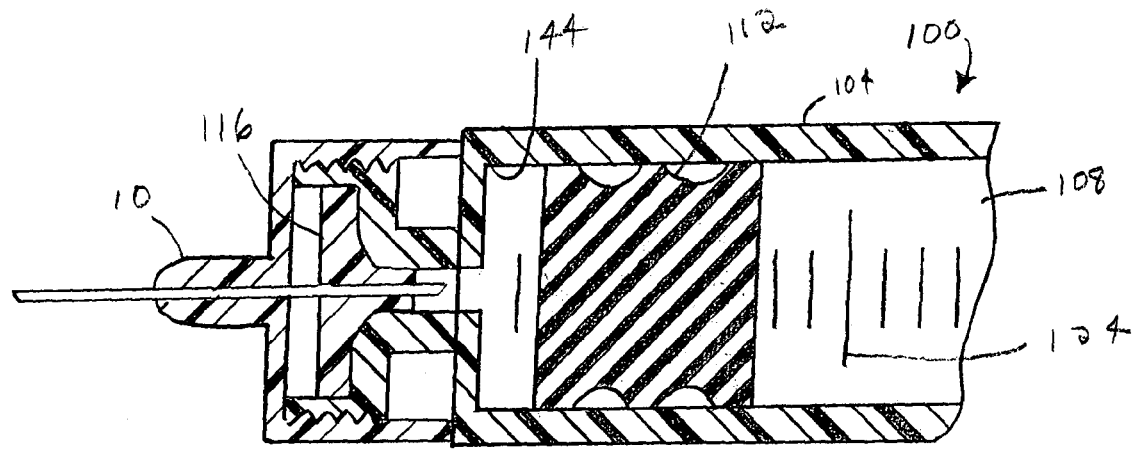
FIG. 14 is a partial cross-sectional view illustrating a reduced dead volume feature of a cartridge in accordance with an embodiment of the present invention.
Figure 15:
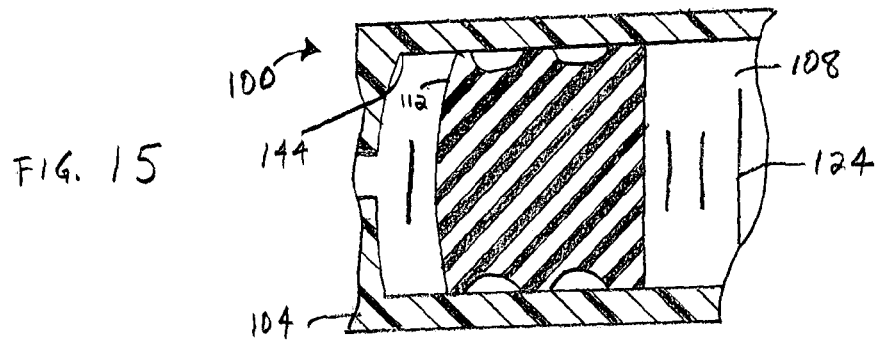
FIG. 15 is a partial cross-sectional view illustrating an embodiment of a reduced dead volume feature in accordance with another embodiment of the present invention.

FIG. 14 illustrates an embodiment in which the shape of the leading edge (or leading face) of the stopper closely corresponds to the shape of the end 144 of the interior cavity 108 closest to the septum 116. For example, as shown in FIG. 14, the shape of both the end 144 and the stopper 112 are substantially right angles. Accordingly, the stopper 112 can be moved until it contacts the end 144, thereby minimizing an uninjectable or dead volume of medicament. Similarly, in the embodiment shown in FIG. 15, the shape of the end 144 and the stopper 112 are curved. More specifically, the stopper has a convex curve and the end 144 has as concave curve. One skilled in the art will appreciate the curves of the stopper 112 and the end 144 may be inverted without departing from the scope of the invention. Similarly, one skilled in the art will appreciate that the stopper and the end may have compound curves and/or straight portions without departing from the scope of the present invention. What is desired is that the shape of the stopper 112 corresponds to the shape of the end 144. In addition, according to one embodiment, a small nub or projection is disposed on the face of the stopper so that it enters the narrow nozzle area of the syringe and ejects all of the fluid in the dead space.

Figure 16:
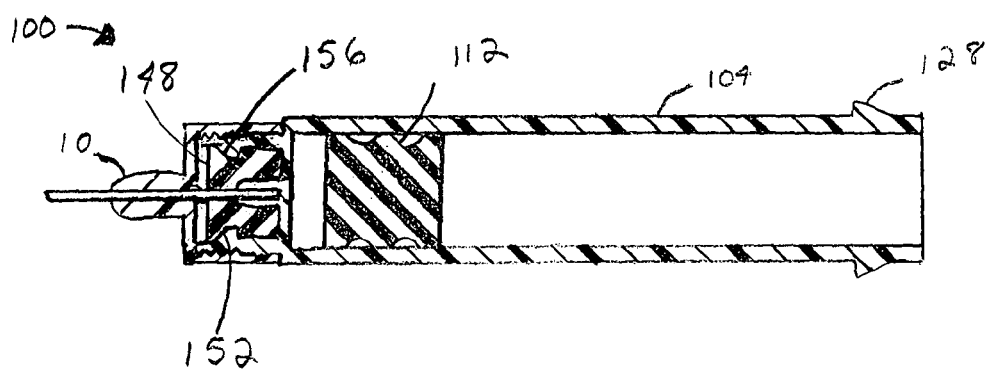
FIG. 16 is a cross-sectional view illustrating a septum for a cartridge in accordance with an embodiment of the present invention.

FIG. 16 illustrates an embodiment in which a septum 148 is inserted into an end of the cartridge body during manufacture of the cartridge 100. An example of a material for the septum 148 includes rubber. As shown in FIG. 16, the cartridge body 104 has a male protrusion 152 and the septum 148 has a corresponding female recess 156 to provide a snap-fit connection between the septum 148 and the cartridge body 104. To assemble the cartridge 100, the manufacturer inserts the septum into the end of the cartridge body 104 until the male protrusion 152 engages the female recess 156, thereby retaining the septum 148 in the cartridge body 104. It will be appreciated by one skilled in the art that the male protrusion 152 may be disposed on the septum 148 and the corresponding female recess 156 may be disposed on the cartridge body 104 without departing from the scope of the invention. One skilled in the art will also appreciate that corresponding pluralities of male protrusions and female recess may be employed without departing from the scope of the present invention. Similar to the septum 116 described above, the septum 148 obviates the need for a crimping ring, such as crimping ring 94, and therefore eliminates the chance of particles entering the interior cavity 108 during a crimping process.

Lyophilization is a dehydration process used to preserve a material, such a medicament, and/or ease transportation of the medicament. During lyophilization, a liquid medicament is first frozen by lowering the temperature below the medicament's triple point (the lowest temperature at which the medicament can exist in a liquid phase). Subsequently, the pressure is lowered and the temperature is raised enough for the frozen water in the medicament to sublime directly from the solid phase to the gas phase. Subsequently, the lyophilized medicament can be reconstituted by adding water.

Some factors of the lyophilization process are the convection (energy to sublimate the material), the ability to remove water vapor, and the packing density of containers in the lyophilization chamber for cycle time optimization (batch process). Some improvements to the process can be achieved by the use of specific materials (such as plastic) to increase the water vapor transmission or by the use of a coating to increase the convection factor, thereby improving the cycle time of the lyophilization.

To use a known cartridge, such as cartridge 76, as a primary container during lyophilization, and thereby avoid having to use multiple containers, a separate vial stopper is employed in addition to the stopper 84. Such a vial stopper has a least a partial length groove. In use, the vial stopper is partially (removably) inserted into the interior cavity of the cartridge 76 so that the vial stopper groove communicates between the interior cavity and the outside of the cartridge 76, to provide a path for escape of sublimated water vapor. At the end of the lyophilization process, the vial stopper is removed and the stopper 84 is inserted into the interior cavity of the cartridge 76.

For medicament stability reasons, each medicament may require a specific formulation of, for example, rubber for the vial stopper. This adds to the complexity of design, because each vial stopper formulation needs to be validated.

Figure 17:
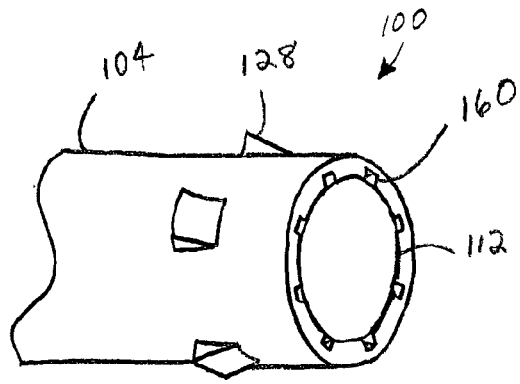
FIG. 17 is a perspective view of a first embodiment of a lyophilization feature for a cartridge in accordance with an embodiment of the present invention.

FIGS. 17-23 illustrate embodiments of the present invention in which a single stopper, such as stopper 112, can be employed with a single container (cartridge body 104) during a lyophilization process. For example, FIG. 17 is a perspective view of a cartridge body 104 having passageways 160 disposed at a second end of the body 104, opposite to the septum (for example, septum 116 or septum 148). The passageways provide venting from the interior cavity 108 during lyophilization.

Figure 18:
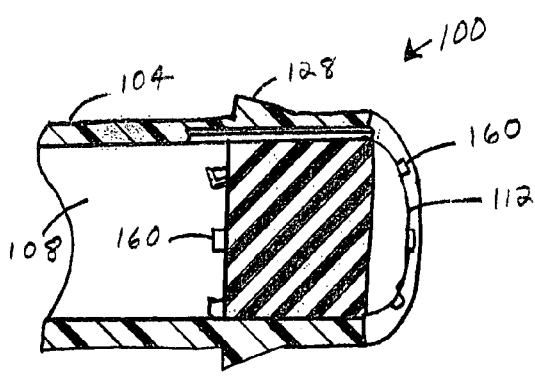
FIG. 18 is a cross-sectional view of the cartridge of FIG. 17.

FIG. 18 is a cross-sectional view of the cartridge 100 of FIG. 17. In FIGS. 17 and 18, the passageways 160 are grooves or slots that axially extend from the second end of the body 104. As shown in FIG. 18, the slots 160 have an axial length greater than that of the stopper 112. Thus, after full insertion of the stopper 112, the slots 160 provide communication between the interior cavity 108 and the outside of the cartridge body 104 to provide venting during the lyophilization process. At the end of the lyophilization cycle, the stopper 112 is further inserted into the interior cavity toward the septum (116 or 148) so that the leading edge of the stopper (closest to the septum) is closer to the septum than the slots 160, thereby sealing or closing off the passageways 160. Such passageways 160 can reduce the time required for the lyophilization process because the stopper 112 is only inserted further, rather than being replaced.

Figure 19:
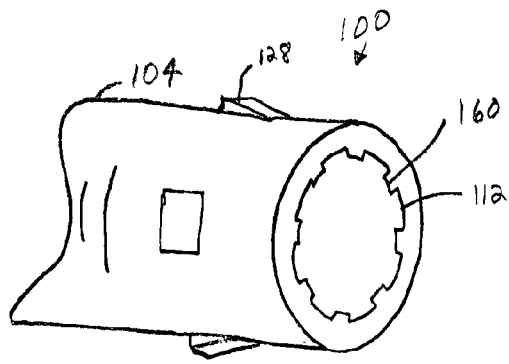
FIG. 19 is a perspective view of a second embodiment of a lyophilization feature for a cartridge in accordance with an embodiment of the present invention.
Figure 20:
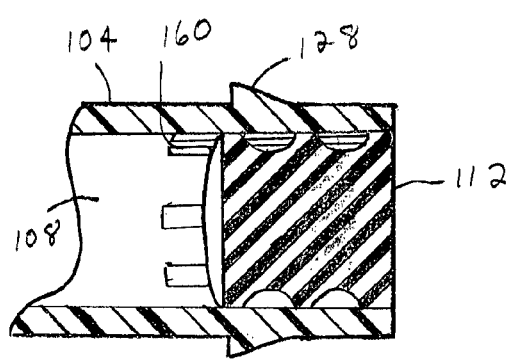
FIG. 20 is a cross-sectional view of a third embodiment of a lyophilization feature for a cartridge in accordance with an embodiment of the present invention.
Figure 21:
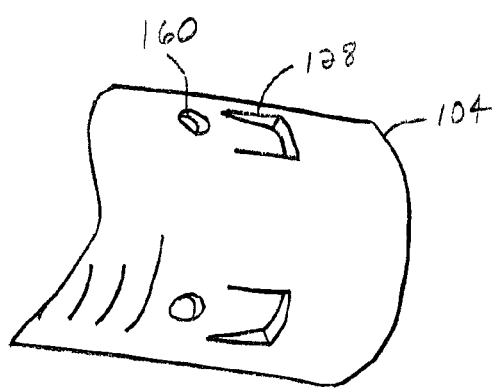
FIG. 21 is a perspective view of a fourth embodiment of a lyophilization feature for a cartridge in accordance with an embodiment of the present invention.

FIG. 19 illustrates an embodiment in which the passageways 160 are ribs 160 extending radially inwardly from an internal surface of the cartridge body 104. In FIG. 20, the passageways 160 are slots 160 extending radially through the wall of the cartridge body. FIG. 21 illustrates an embodiment in which the passageways 160 are holes extending radially through the wall of the cartridge body 104. One skilled in the art will appreciate that the passageways may be straight or may be curved without departing form the scope of the present invention.

Figure 22:
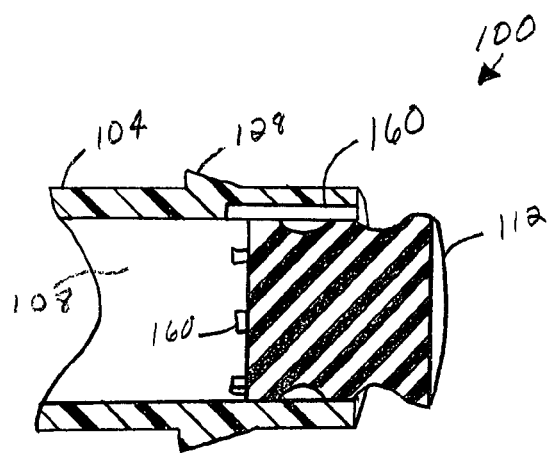
FIGS. 22 and 23 are cross-sectional views of a fifth embodiment of a lyophilization feature for a cartridge in accordance with an embodiment of the present invention.
Figure 23:
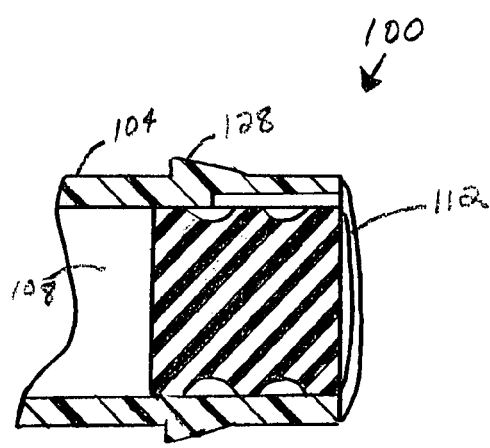

FIGS. 22 and 23 illustrate an embodiment in which the passageways 160 are slots 160 that extend from the second end of the cartridge body 104 and have an axial length that is less than that of the stopper 112. As shown in FIG. 22, the slots 160 provide venting from the interior cavity directly to an outside of the cartridge body 104 when the stopper 112 is partially inserted into the interior cavity 108. And as illustrated in FIG. 23, full insertion of the stopper 112 into the interior cavity 108 closes off the passageways 160.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of the appended claims and equivalents thereof.

The invention claimed is:

1. A cartridge for containing and dispensing a medicament, the cartridge comprising:
a cartridge body having an interior cavity therein;
a stopper movably disposed within the interior cavity;
a septum disposed at an opposite end of the interior cavity from the stopper for containing a medicament within the interior cavity;
a connection thread integrally formed as a unitary construction with the cartridge body, the thread being disposed at a first end of the cartridge body for connecting a pen needle directly to the cartridge body to pierce the septum and provide communication between the medicament and a patient end of the pen needle; and
a connector for directly connecting the cartridge body to a dosing mechanism for moving the stopper toward the septum to dispense the medicament,
wherein the cartridge body comprises at least one passageway for venting the interior cavity during lyophilization when the stopper is partially inserted into the interior cavity, the at least one passageway comprising a slot recessed from a surface of the interior cavity, the slot axially extending from a second end of the cartridge body opposite to the first end and having an axial length less than that of the stopper.

2. The cartridge according to claim 1, wherein the septum is adhered directly to the cartridge body.

3. The cartridge according to claim 1, wherein the cartridge body comprises a plastic material that does not react with the medicament.

4. The cartridge according to claim 3, wherein the cartridge body comprises cyclic olefin polymer (COP) or cyclic olefin copolymer (COC).

5. The cartridge according to claim 3, wherein the septum comprises an elastomeric material that does not react with the medicament and is adhered directly to the cartridge body.

6. The cartridge according to claim 1, further comprising dosage indicia disposed directly on the cartridge body.

7. The cartridge according to claim 6, wherein the dosage indicia comprise ink printed directly on the cartridge body.

8. The cartridge according to claim 6, wherein the dosage indicia comprise etched indicia.

9. The cartridge according to claim 6, wherein:
the cartridge body comprises a plastic material that does not react with the medicament; and
the dosage indicia comprise an additive in the plastic material released by laser etching.

10. The cartridge according to claim 6, wherein the dosage indicia are etched into a mold to be formed on the cartridge body during molding thereof.

11. The cartridge according to claim 6, wherein the stopper is visible through a wall of the cartridge body and the progress of the stopper within the interior cavity with respect to the dosage indicia indicates a remaining volume of medicament.

12. The cartridge according to claim 1, wherein the connector comprises:
a male protrusion disposed on one of the cartridge body and the dosing mechanism; and
a corresponding female recess disposed on the remaining one of the cartridge body and the dosing mechanism.

13. The cartridge according to claim 12, wherein the male protrusion comprises a wedge shape for providing a snap fit.

14. The cartridge according to claim 12, wherein:
the male protrusion comprises a substantially axially aligned linear protrusion; and
the female recess comprises one of a substantially axially aligned slot and an L-shaped slot having a substantially axially aligned portion and a radial portion.

15. The cartridge according to claim 12, wherein:
the male protrusion comprises at least one male thread; and
the female recess comprises at least one female thread.

16. The cartridge according to claim 12, further comprising an anti-disassembly feature.

17. The cartridge according to claim 16, wherein the anti-disassembly feature comprises:
a ratchet disposed on one of the cartridge body and the dosing mechanism; and
at least one tooth disposed on the remaining one of the cartridge body and the dosing mechanism.

18. The cartridge according to claim 1, wherein an end of the stopper closest to the septum has a shape corresponding to a shape of an end of the interior cavity closest to the septum for minimizing an uninjectable volume of medicament.

19. The cartridge according to claim 18, wherein the shape of the end of the stopper and the shape of the end of the interior cavity comprise a substantially right angle.

20. The cartridge according to claim 18, wherein the shape of the end of the stopper and the shape of the end of the interior cavity comprise a curved shape.

21. A cartridge for containing and dispensing a medicament, the cartridge comprising:
a cartridge body having an interior cavity therein;
a stopper movably disposed within the interior cavity;
a septum disposed at an opposite end of the interior cavity from the stopper for containing a medicament within the interior cavity;
a connection thread integrally formed as a unitary construction with the cartridge body, the thread being disposed at a first end of the cartridge body for connecting a pen needle directly to the cartridge body to pierce the septum and provide communication between the medicament and a patient end of the pen needle; and
a connector for directly connecting the cartridge body to a dosing mechanism for moving the stopper toward the septum to dispense the medicament,
wherein the cartridge body comprises at least one passageway for venting the interior cavity during lyophilization subsequent to at least partial insertion of the stopper into the interior cavity, the passageway comprising a slot recessed from a surface of the interior cavity, the slot axially extending directly to an outside of the cartridge body at a second end of the cartridge body opposite to the first end and having an axial length less than that of the stopper.

22. A cartridge for containing and dispensing a medicament, the cartridge comprising:
a cartridge body having an interior cavity therein;
a stopper movably disposed within the interior cavity;
a septum disposed at an opposite end of the interior cavity from the stopper for containing a medicament within the interior cavity; and
a connection thread integrally formed as a unitary construction with the cartridge body, the thread being disposed at a distal end of the cartridge body for connecting a pen needle directly to the cartridge body to pierce the septum and provide communication between the medicament and a patient end of the pen needle;
wherein the cartridge body comprises at least one passageway for venting the interior cavity during lyophilization subsequent to at least partial insertion of the stopper into the interior cavity, the passageway comprising a slot recessed from a surface of the interior cavity, the slot axially extending from a proximal-most edge of the cartridge body and having an axial length less than that of the stopper.

* * * * *